United States Patent [19]
Vanlerberghe et al.

[11] 4,371,517
[45] Feb. 1, 1983

[54] COMPOSITION FOR TREATING FIBROUS MATERIALS, BASED ON CATIONIC AND ANIONIC POLYMERS

[75] Inventors: Guy Vanlerberghe, Villevaude; Henri Sebag; Alexandre Zysman, both of Paris; Claude Dubief, Guyancourt, all of France

[73] Assignee: L'Oreal, Paris, France

[21] Appl. No.: 75,197

[22] Filed: Sep. 12, 1979

[30] Foreign Application Priority Data

Sep. 13, 1978 [FR] France .............. 78 26343

[51] Int. Cl.³ .............. A61K 7/06; D06M 9/00
[52] U.S. Cl. .............. 424/70; 8/115.7; 8/127.5; 8/127.51
[58] Field of Search .............. 424/70, DIG. 2; 8/127.51, 115.7, 127.5

[56] References Cited

U.S. PATENT DOCUMENTS

| | | | |
|---|---|---|---|
| 3,227,615 | 1/1966 | Korden | 424/71 |
| 3,929,990 | 12/1975 | Green et al. | 424/78 |
| 3,958,581 | 5/1976 | Abegg et al. | 424/DIG. 2 |
| 3,966,404 | 6/1976 | Papantoniou et al. | 8/127.51 |
| 3,966,904 | 6/1976 | Green et al. | 424/78 |
| 4,009,256 | 2/1977 | Nowak, Jr. et al. | 424/DIG. 2 |
| 4,027,008 | 5/1977 | Sokol | 8/127.51 X |
| 4,157,388 | 6/1979 | Christiansen | 8/127.5 X |
| 4,172,887 | 10/1979 | Vanlerberghe et al. | 8/127.51 X |
| 4,240,450 | 12/1980 | Grollier et al. | 132/7 |

FOREIGN PATENT DOCUMENTS

| | | |
|---|---|---|
| 1228060 | 4/1971 | United Kingdom. |
| 1437912 | 6/1976 | United Kingdom. |

*Primary Examiner*—Ethel G. Love
*Attorney, Agent, or Firm*—Fleit & Jacobson

[57] ABSTRACT

The invention provides compositions intended for the treatment of fibrous materials. These compositions contain at least one cationic polymer, at least one anionic polymer, at least one alkali metal salt and at least one non-ionic surface-active agent or surface-active agent which contains one or more carboxyl or carboxylate groups in addition to non-ionic groups.

15 Claims, No Drawings

COMPOSITION FOR TREATING FIBROUS MATERIALS, BASED ON CATIONIC AND ANIONIC POLYMERS

DESCRIPTION

The present invention relates to compositions based on polymers, which are intended to be used in the treatment of fibres, in particular hair or textile fibres. It relates more particularly to compositions for washing or dyeing these materials.

Numerous compositions, in particular cosmetic compositions, containing either anionic polymers or cationic polymers, are known, the purpose of which is to modify the properties of the materials treated.

We have discovered that it is very advantageous to treat fibrous materials with compositions which simultaneously contain one or more anionic polymers, one or more cationic polymers, alkali metal salts and one or more non-ionic surface-active agents or surface-active agents which contain one or more carboxyl or carboxylate groups in addition to non-ionic groups i.e. a non-ionic surface-active molecule which is substituted by one or more carboxyl or carboxylate groups.

In fact, by using this combination, it is possible to impart, for example to hair, softness and ease of comb-out at the same time as waveset hold, strength or gloss. Textile fibres treated with this combination also possess valuable properties of softness and good hold.

These compositions exhibit the advantage of being homogeneous and stable; when they are diluted with water on rinsing the hair or textile materials, they produce a deposit of polymers on these materials.

In certain cases, the problem of the solubilisation of the precipitate which can form can be solved by the use of an appropriate solubilising agent, such as an organic solvent or anionic surface-active agent, and by suitably adjusting the pH. We have discovered that, by using, according to the present invention, alkali metal salts and non-ionic surface-active agents or surface-active agents which contain one or more carboxyl or carboxylate groups in addition to non-ionic groups, it is possible to obtain compositions which are homogeneous and stable at a pH which is lower than that required when using only the above-mentioned solubilising agents, and is substantially closer to neutrality, preferably from 5 to 8, which compositions are capable of producing a deposit of polymers on dilution with water.

The present invention therefore provides a composition which is suitable for use, and intended to be used, in the treatment of hair and textile fibres and which contains at least one anionic polymer, at least one cationic polymer, at least one alkali metal salt and at least one non-ionic surface-active agent or surface-active agent which contains one or more carboxyl or carboxylate groups in addition to non-ionic groups.

The present invention also provides a process for treating hair or textile materials, which employs a composition of this invention.

The composition of the present invention generally has a pH of 5 to 8.

The cationic and anionic polymers are preferably each present in an amount of 0.25 to 3% by weight, the alkali metal salt is present in an amount of 0.25 to 8% by weight and the said surface-active agent is present in an amount of 1 to 50% by weight, preferably 5 to 25% by weight.

The ratios of the said cationic polymer to the anionic polymer, present in the compositions according to the invention, are preferably from 5 to 0.4, in particular from 3 to 0.5, expressed as the ratio of equivalents of cationic units to equivalents of anionic units.

The alkali metal salts which are particularly preferred according to the invention are sodium, potassium or lithium salts. These salts are preferably chosen from amongst halides, such as chloride and bromide, sulphates, or salts of organic acids, such as acetates or lactates.

The anionic polymers which are particularly preferred according to the invention are polymers which must be soluble in water after neutralisation of the acid groups with an alkali, such as sodium hydroxide or potassium hydroxide, or an amine, such as triethanolamine, 2-amino-2-methylpropan-1-ol or 2-amino-2-methylpropane-1,3-diol, in the presence of the above-mentioned alkali metal salts and surface-active agents, in proportions by weight of, for example 1/0.25 to 8/3 to 30.

Anionic polymers which can be used according to the invention include polymers which contain several carboxylic acid groups in their chain.

The carboxylic acid groups are generally provided by unsaturated mono- or di-carboxylic acid, as monomers, such as those corresponding to the formula

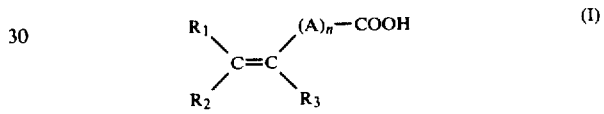

in which n is 0 or an integer from 1 to 10, A denotes a methylene group joined to the carbon atom of the unsaturated group and/or to the adjacent methylene group if n is greater than 1, either directly or via a hetero-atom, such as oxygen or sulphur, $R_1$ denotes a hydrogen atom or a phenyl or benzyl group, $R_2$ denotes a hydrogen atom or a lower alkyl or carboxyl group and $R_3$ denotes a hydrogen atom, a lower alkyl group, a $CH_2$-COOH group or a phenyl or benzyl group.

In the above-mentioned formula, a lower alkyl radical preferably denotes a group having 1 to 4 carbon atoms, in particular methyl or ethyl.

The preferred anionic polymers according to the invention are:

homopolymers or copolymers of acrylic or methacrylic acid, in particular the products sold under the names VERSICOL E or K by ALLIED COLLOID or the name ULTRAHOLD 8 by CIBA GEIGY; the copolymers of acrylic acid and acrylamide sold in the form of their sodium salt under the names RETEN 421, 423 or 425 by HERCULES; and the acrylic or methacrylic acid-vinyl alcohol copolymers sold under the name HYDAGEN F by HENKEL;

copolymers of the above-mentioned acids with an unsaturated monoethylenic monomer, such as ethylene, vinylbenzene, vinyl and allyl esters and acrylic or methacrylic acid esters, which copolymers are optionally grafted to a polyalkylene glycol, such as polyethylene glycol, and optionally crosslinked. Such polymers are described, in particular, in French Pat. No. 1,222,944 and German Application No. 2,330,956; copolymers of this type containing, in their chain, an optionally N-alkylated and/or -hydroxyalkylated acrylamide unit, such as described, in particular, in Luxembourg Patent application Nos. 75,370 and 75,371, or sold under the name QUADRAMER 5 by American Cyanamid;

copolymers derived from crotonic acid, such as those containing, in their chain, vinyl acetate or propionate units and optionally units from other monomers, such as an allyl or methallyl ester, a vinyl ether or a vinyl ester of a saturated carboxylic acid having a long hydrocarbon chain, such as those containing at least 5 carbon atoms, it being possible for these polymers to be optionally grafted and crosslinked. Such polymers are described, inter alia, in French Pat. Nos. 1,222,944, 1,580,545, 2,265,782, 2,265,781 and 1,564,110. Commercial products belonging to this class are the resins 28-29-30 and 26-13-14 sold by the Société National Starch; and polymers derived from maleic, fumaric and itaconic acid or anhydride with vinyl esters, vinyl ethers, vinyl halides, phenylvinyl derivatives and acrylic acid and its esters, which polymers are described, in particular, in U.S. Pat. Nos. 2,047,398, 2,723,248 and 2,102,113 and British Patent Specification No. 837,805, and especially those sold under the names GANTREZ AN or ES by General Anilin or the name EMA 1325 by MONSANTO; polymers which also belong to this class are the copolymers, described in French Patent application Nos. 76/13,929 and 76/20,917, of maleic, citraconic or itaconic anhydride and an allyl or methallyl ester optionally containing an acrylamide or methacrylamide group in their chain, which is monoesterified or monoamidated.

The cationic polymers are polymers of the polyamine or quaternary polyammonium type, the amine or ammonium group either forming part of the polymer chain or being joined to the latter.

Polymers of this type which can be used according to the invention include, vinylpyrrolidone/aminoalcohol acrylate copolymers (which may or may not be quaternised), such as those sold under the name GAFQUAT, for example "GAFQUAT 734 or 755", by the GAF Corp., which are described in greater detail, in particular, in French Pat. No. 2,077,143, cellulose ether derivatives containing quaternary ammonium groups, such as those described in French Pat. No. 1,492,597, and, in particular, the polymers sold under the name JR, such as JR-125, JR-400 and JR-30M, by UNION CARBIDE CORPORATION.

Cationic polymers which give particularly valuable results include:

(1) water-soluble cyclic polymers having a molecular weight of 20,000 to 3,000,000, such as polymers containing units corresponding to the formula (II) or (II'):

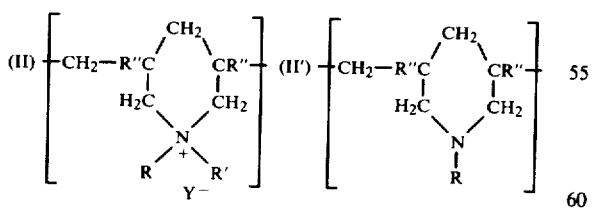

in which R" denotes hydrogen or methyl, R and R' independently of one another denote an alkyl group having from 1 to 22 carbon atoms, a hydroxyalkyl group in which the alkyl group preferably has 1 to 5 carbon atoms, or a lower amidoalkyl group, or R and R' together denote, together with the nitrogen atom to which they are attached, a heterocyclic group such as piperidinyl or morpholinyl, and Y is an anion such as bromide, chloride, acetate, borate, citrate, tartrate, bisulphate, bisulphite, sulphate or phosphate.

Amongst the quaternary ammonium polymers of the type defined above, those which are more particularly preferred are the dimethyldiallylammonium chloride homopolymers having a molecular weight of less than 100,000 which are sold under the name MERQUAT 100, and the copolymers of dimethyldiallylammonium chloride and acrylamide, having a molecular weight of more than 500,000 which are sold under the name MERQUAT 550 by MERCK.

These cyclic polymers are described in French Pat. No. 2,080,759 and its Certificate of Addition No. 2,190,406.

(2) homopolymers or copolymers derived from acrylic or methacrylic acid and containing the unit:

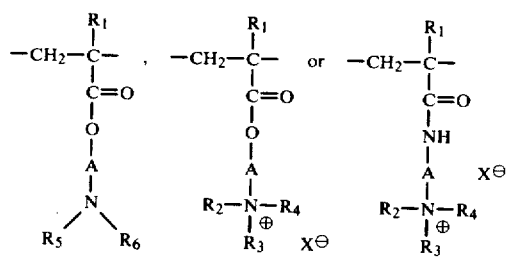

in which $R_1$ is H or $CH_3$, A is a linear or branched alkyl group having 1 to 6 carbon atoms or a hydroxyalkyl group having 1 to 4 carbon atoms, $R_2$, $R_3$ and $R_4$, which are identical or different, denote alkyl groups having 1 to 18 carbon atoms or a benzyl group, $R_5$ and $R_6$ are H or alkyl having 1 to 6 carbon atoms, and $X^-$ denotes a methosulphate anion or a halide anion such as chloride or bromide.

The comonomer or comonomers which can be used include: acrylamide, methylacrylamide, diacetone acrylamide, N-alkylated acrylamide and methacrylamide, lower alkyl acrylates or methacrylates, vinylpyrrolidone and vinyl esters; these can be grafted and or crosslinked, such as those described in French Pat. No. 2,189,434.

Further examples which may be mentioned are:

the copolymers of acrylamide and β-methacryloyloxyethyl-trimethylammonium methosulphate which are sold under the names Reten 205, 210, 220 and 240 by the Société Herculés; and the aminoethyl acrylate phosphate/acrylate copolymers which are sold under the name Catrex by National Starch, and also the products described in U.S. Pat. No. 3,372,149 or the polymers referred to as Quaterniums in the Cosmetic Ingredient Dictionary.

(3) cationic polymers which are:

(a) the polymers of the formula: -A-Z-A-Z- (III), in which A denotes a radical containing two, generally terminal, amino groups, preferably

and Z denotes the symbol B or B'; B and B', which are identical or different, denote a divalent radical which is a straight-chain or branched-chain alkylene radical which contains up to 7 carbon atoms in the main chain, is unsubstituted or substituted by one or more hydroxyl groups and can also contain 1 to 3 aromatic and/or heterocyclic rings in addition to oxygen, nitrogen and sulphur atoms, the oxygen, nitrogen and sulphur atoms being present in the form of an ether, thioether, sulphoxide, sulphone, sulphonium, amino, alkylamino, alkenylamino, benzylamino, amine oxide, quaternary ammonium, amido, imido, alcohol, ester and/or urethane group; these polymers and the process for their preparation are described in French Pat. No. 2,162,025.

(b) the polymers of the formula -A-$Z_1$-A-$Z_1$- (IV), in which A denotes a radical containing two, generally terminal, amine groups, preferably

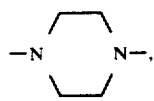

and each $Z_1$ denotes the symbol $B_1$ or $B'_1$ such that $Z_1$ denotes $B'_1$ at least once; $B_1$ denotes a divalent radical which is a straight-chain or branched-chain alkylene or hydroxyalkylene radical having up to 7 carbon atoms in the main chain, and $B'_1$ is a divalent radical which is a straight-chain or branched-chain alkylene radical which has up to 7 carbon atoms in the main chain, is unsubstituted or substituted by one or more hydroxyl radicals and is interrupted by one or more chain nitrogen atoms, the nitrogen atom being substituted by an alkyl chain which optionally has from 1 to 4, preferably 4, carbon atoms, is optionally interrupted by an oxygen atom and obligatorily contains one or more hydroxyl and/or carboxyl groups.

(c) the quaternary ammonium salts and the products resulting from the oxidation of the polymers of the formulae (III) and (IV) indicated above under (a) and (b), generally one in which at least one tertiary amino group in A has been converted into an amine oxide group.

The polymers of the formula (IV) and a process for their preparation are described in French Application No. 2,280,361.

The polymers of the formula -A-Z-A-Z- (III) can be prepared as indicated in French Pat. No. 2,162,025.

(4) the quaternary polyammonium compounds of the formula:

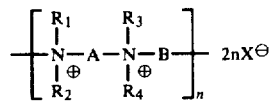

in which $R_1$, $R_2$, $R_3$ and $R_4$, which are identical or different, represent aliphatic, alicyclic or arylaliphatic radicals containing a maximum of 20 carbon atoms, or lower hydroxyaliphatic radicals, or alternatively $R_1$ and $R_2$, and/or $R_3$ and $R_4$, together form, with the nitrogen atom to which they are attached, a heterocyclic ring optionally containing a second hetero-atom other than nitrogen, or alternatively $R_1$, $R_2$, $R_3$ and $R_4$ independently represent a group:

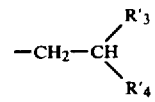

$R'_3$ denoting hydrogen or lower alkyl and $R'_4$ denoting —CN, or

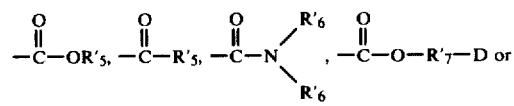

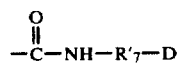

$R'_5$ denoting lower alkyl, $R'_6$ denoting hydrogen or lower alkyl, $R'_7$ denoting alkylene and D denoting a quaternary ammonium group, A and B represent polymethylene groups which contain from 2 to 20 carbon atoms, can be linear or branched and saturated or unsaturated, and can contain, in the main chain, one or more aromatic rings, to provide a group such as

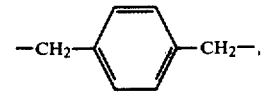

or one or more groups Y to provide a group —CH$_2$—Y—CH$_2$—, in which Y denotes O, S, SO, SO$_2$,

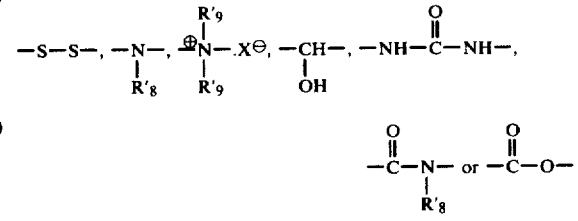

$X^\ominus$ denoting an anion derived from an inorganic or organic acid, $R'_8$ denoting hydrogen or lower alkyl and $R'_9$ denoting lower alkyl, or alternatively A and $R_1$ and $R_3$ form a piperazine ring together with the two nitrogen atoms to which they are attached, and B can also denote a group: —(CH$_2$)$_n$CO—D—OC—(CH$_2$)$_n$—, in which D denotes:

(a) a glycol radical of the formula —O—Z—O—, in which Z denotes a linear or branched hydrocarbon radical or a group corresponding to the formula:

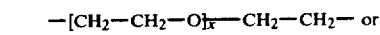

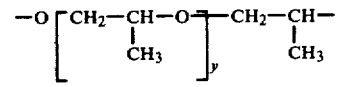

in which x and y denote an integer from 1 to 4, representing a particular degree of polymerisation (in a given molecule), or any number from 1 to 4, representing a mean degree of polymerisation (in the product);

(b) a bis-secondary diamine radical, such as a piperazine derivative of the formula:

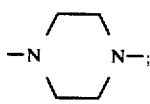

(c) a bis-primary diamine radical of the formula: —NH—Y—NH—, in which Y denotes a linear or branched hydrocarbon radical or the divalent radical —CH$_2$—CH$_2$—S—S—CH$_2$—CH$_2$—, or (d) a ureylene group of the formula —NH—CO—NH—, X$^\ominus$ is an anion, such as chloride or bromide, and n is such that the molecular weight is between 1,000 and 100,000.

Polymers of this type are described, in particular, in French Pat. Nos. 2,320,330 and 2,270,846, French Applications Nos. 76/20,261 and 2,336,434 and U.S. Pat. Nos. 2,273,780, 2,375,853, 2,388,614, 2,454,547, 3,206,462, 2,361,002 and 2,271,378, which are hereby incorporated by reference.

Other polymers of this type are described in U.S. Pat. Nos. 3,874,870, 4,001,432, 3,929,990, 3,966,904, 4,005,193, 4,025,617, 4,025,627, 4,025,653, 4,026,945 and 4,027,020, which are hereby incorporated by reference.

(5) optionally alkylated, crosslinked polyaminoamides which are water-soluble and can be obtained by cross-linking a polyamino-polyamide (A), prepared by the polycondensation of an acid compound with a polyamine. The acid compound is, for example, (i) an organic dicarboxylic acid, (ii) an aliphatic mono- or dicarboxylic acid having an ethylenic double bond, (iii) an ester of the abovementioned acids, preferably the esters of lower alkanols having from 1 to 6 carbon atoms, and (iv) mixtures of two or more of these compounds. The polyamine may be a bis-primary or mono- or di-secondary polyalkylene-polyamine. Up to 40 or 50 mol % of this polyamine can be replaced by a bis-primary amine, preferably ethylene-diamine, or by a bis-secondary amine, preferably piperazine, and up to 20 mol % can be replaced by hexamethylene-diamine. The crosslinking can be effected by a crosslinking agent (B) which is an epihalogenohydrin, diepoxide, dianhydride, unsaturated anhydride or bis-unsaturated derivative, the crosslinking is generally carried out using 0.025 to 0.35 molecule of crosslinking agent per amine group of the polyaminopolyamide (A), preferably from 0.025 to 0.2 and in particular from 0.025 to 0.1 molecule of crosslinking agent per amine group of the polyamino-polyamide (A). These polymers and their preparation are described in greater detail in French Patent Application No. 2,252,840.

Such crosslinked polymers are perfectly soluble in water at a concentration of 10% by weight without forming a gel, and the viscosity of a 10% by weight solution in water at 25° C. is at least 3 centipoises and usually from 3 to 200 centipoises.

The crosslinked and optionally alkylated polyaminoamides do not contain any reactive groups, do not have any alkylating properties and are chemically stable.

The polyaminoamides (A) themselves can also be used in the compositions of this invention.

(6) the water-soluble, crosslinked polyaminoamides obtained by crosslinking a polyaminoamide, (A, described above) by means of a crosslinking agent which is:

(I) a compound which is (1)a bis-halogenohydrin, (2)a bis-azetidinium compound, (3)a bis-halogenoacyl derivative of a diamine, and (4)a bis-(alkyl halide);

(II) an oligomer obtained by reacting a compound (a), which is (1)a bis-halogenohydrin, (2)a bis-azetidinium compound, (3)a bis-halogenoacyl derivative of a diamine, (4)a bis-(alkyl halide), (5) an ephihalogenohydrin, (6) a diepoxide, or (7) bis-unsaturated derivative, with a compound (b) which is a difunctional compound which is reactive towards the compound (a); and (III) the product resulting from the quaternisation of a compound (a) or an oligomer (II) and contains one or more tertiary amine groups which can be totally or partially alkylated with an alkylating agent (c), preferably methyl or ethyl chloride, bromide, iodide, sulphate, mesylate or tosylate, benzyl chloride or bromide, ethylene oxide, propylene oxide or glycidol, the crosslinking generally being effected with 0.025 to 0.35 molecule, in particular 0.025 to 0.2 molecule and more particularly 0.025 to 0.1 molecule, of crosslinking agent per amine group of the polyaminoamide.

These crosslinking agents and these polymers, and also the process for their preparation, are described in French Application No. 2,368,508 which is hereby incorporated by reference.

(7) the water-soluble polyaminoamide derivatives resulting from the condensation of polyalkylene-polyamines with polycarboxylic acids, followed by alkylation with a difunctional agent, such as adipic acid/dialkylaminohydroxyalkyl-dialkylenetriamine copolymers, in which the alkyl radical contains 1 to 4 carbon atoms and preferably denotes methyl, ethyl or propyl, which are described in French Patent 1,583,363.

Compounds which make it possible to obtain valuable results are the adipic acid/dimethylaminohydroxypropyl-diethylenetriamine copolymers sold under the name Cartarétine F, F$_4$ or F$_8$ by SANDOZ.

(8) the polymers obtained by reacting a polyalkylene-polyamine, containing two primary amine groups and at least one secondary amine group, with a dicarboxylic acid which is diglycolic acid or a saturated aliphatic dicarboxylic acid having 3 to 8 carbon atoms, the molar ratio of the polyalkylenepolyamine to the dicarboxylic acid being from 0.8:1 to 1.4:1, and reacting the resulting polyamide with epichlorohydrin in a molar ratio of epichlorohydrin to the secondary amine group of the polyamide of from 0.5:1 to 1.8:1; these polymers are disclosed in U.S. Pat. Nos. 3,227,615 and 2,961,347, which are hereby incorporated by reference.

Particularly valuable polymers are those which are sold under the name HERCOSETT 57 by Hercules Incorporated and have a viscosity of 30 cps at 25° C. in a 10% by weight aqueous solution, and those sold under the name PD 170 or DELSETTE 101 by Hercules, which is an adipic acid/epoxypropyldiethylenetriamine copolymer.

(9) polyalkyleneimines, in particular the polyethyleneimines described in greater detail in U.S. Pat. Nos. 2,182,306, 2,553,696, 2,806,838 and 2,208,085, and also the alkylated or alkoxylated derivatives described in U.S. Pat. No. 2,039,151 and French Pat. No. 1,506,349.

Amongst the polyethyleneimines and their derivatives, there may be mentioned the products sold under the names PEI 6, PEI 12, PEI 18, PEI 300, PEI 600, PEI 1200, PEI 1800 and PEI 600 E, the last being a polyethyleneimine alkylated with ethylene oxide in a ratio of 1:0.75, and the names TYDEX 14 and TYDEX 16, the latter having a density of about 1.06 and a viscosity at 25° C. of more than 1,000 cps. These polyethyleneimines are sold by DOW CHEMICAL. The various patents mentioned above are hereby incorporated by reference.

Other polyethyleneimines which can be used according to the invention are those sold by BASF under the name POLYMIN P, which has a density $d_{20}$ of about 1.07 and a Brookfield viscosity of 10,000–20,000 in a 50% strength aqueous solution (at 20° C. and 20 rpm), POLYMIN SN, which has a density $d_{20}$ of about 1.06 and a viscosity of 800–1,800 cps in a 20% strength aqueous solution, and POLYMIN HS, which has a density $d_{20}$ of about 1.07 and a viscosity of 500–1,000 cps in a 20% strength aqueous solution.

The products resulting from the reaction of polyethyleneimine with ethyl formate, described in French Pat. No. 2,167,801, can also be used.

(10) the water-soluble polymers resulting from the condensation of a polyamine and epichlorohydrin, such as the product resulting from the condensation of tetraethylenepentamine and epichlorohydrin.

(11) the quaternary polyureylenes of the type described in Belgian Pat. No. 77/3,892.

Amongst the non-ionic surface-active agents which are preferably used in the compositions according to the invention, there may be mentioned the products resulting from the condensation of a monoalcohol, an alpha-diol, an alkylphenol or an alkanolamide, such as diglycolamide, with glycidol, such as the products corresponding to the formula: $R_4$—CHOH—CH$_2$—O—(CH$_2$—CHOH—CH$_2$—O)$_p$H in which $R_4$ denotes an aliphatic, cycloaliphatic or arylaliphatic radical preferably having 7 to 21 carbon atoms, and mixtures thereof, it being possible for the aliphatic chains to contain ether, thioether or hydroxymethylene groups, and in which p is a number from 1 to 10 inclusive, which compounds are described in French Patent 2,091,516; products corresponding to the formula:

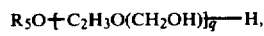

in which $R_5$ denotes an alkyl, alkenyl or alkylaryl radical and q has a value from 1 to 10 inclusive; and products corresponding to the formula:

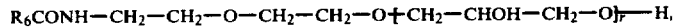

in which $R_6$ denotes a linear or branched, saturated or unsaturated, aliphatic radical, or a mixture of such radicals, which can optionally contain one or more hydroxyl groups, which have from 8 to 30 carbon atoms and can be of natural or synthetic origin, and r denotes an integer or decimal from 1 to 5. It will be appreciated that p q and r generally represent an average value corresponding to the average degree of condensation since the condensation usually results in the production of compounds with different chain lengths.

Other compounds belonging to this class are polyoxyethyleneated alcohols or alkylphenols or esters of polyethylene glycol or polyglycerol having a linear or branched fatty chain containing 8 to 18 carbon atoms. There may also be mentioned copolymers of ethylene oxide and propylene oxide, products resulting from the condensation of ethylene oxide and propylene oxide with fatty alcohols, polyoxyethyleneated fatty amides, polyoxyethyleneated fatty amines, polyoxyethyleneated fatty acid esters of sorbitol and polyoxyethyleneated fatty acid esters of sucrose.

Amongst these non-ionic surface-active agents, those which are more particularly preferred correspond to the formula: $R_4$—CHOH—CH$_2$—O—(CH$_2$—CHOH—CH$_2$—O)$_p$H, in which $R_4$ denotes a mixture of alkyl radicals having 9 to 12 carbon atoms and p has a statistical value of about 3.5,

in which $R_5$ denotes $C_{12}H_{25}$ and q has a statistical value of 4 to 5, or

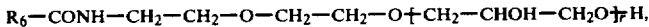

in which $R_6$ denotes a mixture of radicals derived from lauric, myristic and oleic acids and copra acids and r has a statistical value of 3 to 4.

The preferred oxyethyleneated or polyglycerolated fatty alcohols are polyoxyethyleneated oleyl alcohol containing about 10 mols of ethylene oxide, oxyethyleneated lauryl alcohol containing about 12 mols of ethylene oxide, cetyl alcohol oxyethyleneated with 6 to 10 mols of ethylene oxide, cetyl/stearyl alcohol oxyethyleneated with 3 to 10 mols of ethylene oxide, stearyl alcohol containing 2, 10, 15 or 20 mols of ethylene oxide, oxyethyleneated nonylphenol containing about 9 mols of ethylene oxide, oxyethyleneated octylphenol containing about 5.5 mols of ethylene oxide, polyglycerolated oleyl alcohol containing about 4 mols of glycerol, synthetic $C_9$–$C_{15}$ fatty alcohols polyoxyethyleneated with 3 to 12 mols of ethylene oxide, polyoxyethylene stearate containing about 50 mols of ethylene oxide, polyoxyethyleneated sorbitan monolaurate containing about 20 mols of ethylene oxide, and the products resulting from the polycondensation of ethylene oxide and propylene glycol.

Amongst the surface-active agents which can be used which contain one or more carboxyl or carboxylate groups in addition to non-ionic groups, there may be mentioned, in particular, polyglyceryl carboxylates, and the carboxylic acids of polyglycol ether corresponding to the formula Alk-(OCH$_2$—CH$_2$)$_n$—OCH$_2$—CO$_2$H, in which the substituent Alk corresponds to a linear aliphatic chain having from 12 to 18 carbon atoms and in which n is an integer from 5 to 15, these compounds being in the form of the free acid or of their salts, and in particular the products sold under the name AKYPO RLM 100 by CHEMY, such as the product of the formula R—(OCH$_2$CH$_2$)$_x$OCH$_2$COOH, in which R is a mixture of $C_{12}$–$C_{14}$ alkyl radicals and x is equal to 10.

In particular, good effects can be obtained on dyed or bleached hair, the combination according to the invention in fact making it possible to recover the appearance and the condition of natural hair.

The compositions according to the invention are preferably aqueous and can be used as such for the purpose of treating the various fibrous materials mentioned above. However, they can also contain organic solvents such as alkanols having from 1 to 8 carbon atoms, such as ethanol, isopropanol, benzyl alcohol, phenylethyl alcohol and methoxy-, ethoxy-, propoxy- and butoxyethanol, alkylene glycols, such as ethylene glycol, propylene glycol, butylene glycol and diethylene glycol monoethyl ether, and also esters, such as the acetate of ethylene glycol monomethyl ether or monoethyl ether and the esters of fatty acids and lower alcohols, such as isopropyl myristate or palmitate. These solvents are generally present in an amount from 0.5 to 30% by weight.

The compositions can contain, in addition to the abovementioned ingredients, adjuvants which are normally used in compositions for treating textiles or hair.

They can contain, in particular, perfumes, dyestuffs, the purpose of which can be to colour either the composition itself or the hair or the textiles, preservatives, sequestering agents, thickeners, emulsifiers, softeners, synergistic agents and foam stabilisers, depending on the application envisaged.

The dyestuffs used for dyeing the materials treated include oxidative dyestuffs, such as those of the well-known diamine, aminophenol or phenol types, and direct dyestuffs, such as azo dyestuffs, anthraquinone dyestuffs, nitrobenzene dyestuffs, indamines, indoanilines, indophenols as well as other oxidative dyestuffs, such as leuco derivatives of these compounds, these various types of dyestuff being used singly or as a mixture.

The compositions according to the invention are preferably used for washing.

For cosmetic use, they can be in the form of, for example, a shampoo, but also in the form of colouring products, rinsing lotions to be applied before or after shampooing, before or after colouring or bleaching or before or after permanent waving, brushing lotions, styling and restructuring lotions and gels.

The perfumes which can be used in these compositions are cosmetically acceptable perfumes; they are generally present in an amount from 0.1 to 0.5% by weight.

Alkalising or acidifying agents such as acetic, lactic, citric and phosphoric acids and ammonia and mono-di- or tri-ethanolamines can be added to the compositions.

The following Examples further illustrate the present invention; the percentages are indicated by weight unless otherwise stated.

The anionic polymers are 100% neutralised with sodium hydroxide.

EXAMPLE 1

The following composition is prepared: Anionic polymer sold under the name

| | |
|---|---|
| GANTREZ ES 425 | 2.14% |
| Cationic polymer referred to as PAA-R2 | 0.96% |
| Non-ionic surface-active agent referred to as TA-1 | 12.5% |
| NaCl | 4% |
| Water q.s.p. | |

The ratio of equivalents of cationic units to equivalents of anionic units is 3 and the pH is equal to 6.

This homogeneous composition is used as a shampoo; when applied to dirty hair after wetting, it produces a gentle foam.

When wet, the hair is easy to comb out and soft to the touch.

When dry, the hair possesses a good hold, has a smooth and soft feel and is very springy, very bulky and very manageable.

After styling, the hair style is firm and holds well and the hair is glossy.

Similar results are obtained with the compositions illustrated in Table I which follows:

TABLE I

| Example | Anionic polymer | % | Cationic polymer | % | Surface-active agent | % | Alkali metal salt | % | Cationic polymer/anionic polymer equivalents |
|---|---|---|---|---|---|---|---|---|---|
| 2 | GANTREZ ES 425 | 2.04 | PAA - R2 | 0.96 | TA-1 | 12.5 | NaCl | 4 | 0.5 |
| 3 | GANTREZ ES 425 | 1.56 | PAA - R2 | 1.44 | TA-1 | 12.5 | NaCl | 4 | 1 |
| 4 | GANTREZ ES 425 | 1.57 | PAA - R2 | 1.43 | TA-1 | 12.5 | NaCl | 6 | 1 |

EXAMPLE 5

A shampoo having the following composition is prepared:

| | |
|---|---|
| Anionic polymer sold under the name GANTREZ ES 425 | 1.97% |
| Cationic polymer referred to as PAA-1 | 1.03% |
| Non-ionic surface-active agent referred to as TA-1 | 12.5% |
| NaCl | 2% |
| Water qsp 100 | |

The pH is equal to 6 and the ratio of cationic polymer/anionic polymer in equivalents is equal to 0.66. When applied to dirty hair after wetting, the formation of a gentle foam is observed.

When wet, the hair is easy to comb out.

When dry, the hair possesses a good hold and is springy and the head of hair is bulky.

The hair style holds well and the hair is soft.

Similar results are obtained on modifying the proportions of the various polymers in the following manner.

TABLE II

| Example | Anionic polymer | % | Cationic polymer | % | Surface-active agent | % | Alkali metal salt | % | Cationic polymer/anionic polymer equivalents |
|---|---|---|---|---|---|---|---|---|---|
| 6 | GANTREZ ES 425 | 1.67 | PAA - I | 1.33 | TA-1 | 12.5 | NaCl | 4 | 1 |
| 7 | GANTREZ ES 425 | 0.89 | PAA - I | 2.1 | TA-1 | 12.5 | NaCl | 4 | 3 |

TABLE II-continued

| Example | Anionic polymer | % | Cationic polymer | % | Surface-active agent | % | Alkali metal salt | % | Cationic polymer/ anionic polymer equivalents |
|---|---|---|---|---|---|---|---|---|---|
| 8 | GANTREZ ES 425 | 2.15 | PAA - I | 0.85 | TA-1 | 12.5 | NaCl | 4 | 0.5 |

The pH of the compositions of Examples 6 and 7 is equal to 5.9 and 5.7 respectively.

EXAMPLES 9 TO 62

Table III which follows is intended to illustrate other methods of carrying out the present invention.

This table indicates the nature of the anionic polymer, the cationic polymer, the surface-active agent and the alkali metal salt, and the ratio of equivalents of cationic units to equivalents of anionic units. As in the preceding tables, the water added in all cases to make up 100 g is not included in this table.

The compositions used as a shampoo gave similar results to those reported above, in particular as regards the ease of comb-out and the softness of the hair when wet, and the springiness and softness of the hair when dry, and the hair style possesses bulk, firmness and a good hold. All these compositions are homogeneous and stable under normal storage conditions.

TABLE III

| Example No. | POLYMER ANIONIC | % | CATIONIC | % | SURFACE-ACTIVE AGENT | % | ALKALI METAL SALT | % | CATIONIC POLYMER/ ANIONIC POLYMER Equivalents |
|---|---|---|---|---|---|---|---|---|---|
| 9 | GANTREZ ES 425 | 2.5 | AZA - 1 | 0.5 | TA - 1 | 12.5 | NaCl | 4 | 0.5 |
| 10 | GANTREZ ES 425 | 2.16 | AZA - 1 | 0.84 | TA - 1 | 12.5 | NaCl | 4 | 1 |
| 11 | GANTREZ ES 425 | 1.9 | PAA - R1 | 1.1 | TA - 1 | 12.5 | NaCl | 4 | 0.5 |
| 12 | GANTREZ ES 425 | 1.4 | PAA - R1 | 1.6 | TA - 1 | 12.5 | NaCl | 4 | 1 |
| 13 | GANTREZ ES 425 | 0.68 | PAA - R1 | 2.32 | TA - 1 | 12.5 | NaCl | 4 | 3 |
| 14 | GANTREZ ES 425 | 0.89 | PAQ - 1 | 2.1 | TA - 1 | 12.5 | NaCl | 4 | 3 |
| 15 | GANTREZ ES 425 | 2.15 | PAQ - 1 | 0.85 | TA - 1 | 12.5 | NaCl | 4 | 0.5 |
| 16 | GANTREZ ES 425 | 1.68 | PAQ - 1 | 1.32 | TA - 1 | 12.5 | NaCl | 4 | 1 |
| 17 | GANTREZ ES 425 | 1.69 | PAA - RA-1 | 1.3 | TA - 1 | 12.5 | NaCl | 4 | 0.5 |
| 18 | GANTREZ ES 425 | 1.18 | PAA - RA-1 | 1.82 | TA - 1 | 12.5 | NaCl | 4 | 1 |
| 19 | GANTREZ ES 425 | 0.53 | PAA - RA-1 | 2.47 | TA - 1 | 12.5 | NaCl | 4 | 3 |
| 20 | GANTREZ ES 425 | 1.57 | PAA - RA 2 | 1.43 | TA - 1 | 12.5 | NaCl | 4 | 0.5 |
| 21 | GANTREZ ES 425 | 1.06 | PAA - RA 2 | 1.94 | TA - 1 | 12.5 | NaCl | 4 | 1 |
| 22 | GANTREZ ES 425 | 0.46 | PAA - RA 2 | 2.54 | TA - 1 | 12.5 | NaCl | 4 | 3 |
| 23 | GANTREZ ES 425 | 1.5 | PAQ - 2 | 1.5 | TA - 1 | 12.5 | NaCl | 4 | 3 |
| 24 | GANTREZ ES 425 | 2.12 | PAQ - 2 | 0.88 | TA - 1 | 12.5 | NaCl | 4 | 1 |
| 25 | GANTREZ ES 425 | 1.88 | AZA - 2 | 1.12 | TA - 1 | 12.5 | NaCl | 4 | 0.5 |
| 26 | GANTREZ ES 425 | 1.36 | AZA - 2 | 1.84 | TA - 1 | 12.5 | NaCl | 4 | 1 |
| 27 | GANTREZ ES 425 | 0.66 | AZA - 2 | 2.34 | TA - 1 | 12.5 | NaCl | 4 | 3 |
| 28 | GANTREZ ES 425 | 0.46 | PAA - RA 3 | 2.54 | TA - 1 | 12.5 | NaCl | 4 | 3 |
| 29 | GANTREZ ES 425 | 1.06 | PAA - RA 3 | 1.94 | TA - 1 | 12.5 | NaCl | 4 | 1 |
| 30 | GANTREZ ES 425 | 1.57 | PAA - RA 3 | 1.43 | TA - 1 | 12.5 | NaCl | 4 | 0.5 |
| 31 | GANTREZ ES 425 | 0.46 | PAA - RA 3 | 2.54 | TA - 1 | 12.5 | NaCl | 2 | 3 |
| 32 | GANTREZ ES 425 | 1.71 | PAA - 2 | 1.29 | TA - 1 | 12.5 | NaCl | 4 | 0.5 |
| 33 | GANTREZ ES 425 | 1.19 | PAA - 2 | 1.81 | TA - 1 | 12.5 | NaCl | 4 | 1 |
| 34 | GANTREZ ES 425 | 0.54 | PAA - 2 | 2.46 | TA - 1 | 12.5 | NaCl | 4 | 3 |
| 35 | SMA 1,000 | 1.39 | PAQ - 1 | 1.61 | TA - 2 | 10 | NaCl | 4 | 1 |
| 36 | SMA 1,000 | 0.56 | PAQ - 1 | 2.42 | TA - 2 | 10 | NaCl | 4 | 3 |
| 37 | SMA 1,000 | 1.10 | AZA - 1 | 1.9 | TA - 2 | 10 | NaCl | 4 | 0.4 |
| 38 | SMA 1,000 | 1.76 | AZA - 1 | 1.24 | TA - 2 | 10 | NaCl | 4 | 1 |
| 39 | SMA 1,000 | 1.76 | AZA - 1 | 1.24 | polyethylene glycol lauryl ether (11-120E) | 10 | NaCl | 4 | 1 |
| 40 | SMA 1,000 | 1.1 | PAA - 1 | 1.9 | polyethylene glycol lauryl ether (11-120E) | 10 | NaCl | 4 | 1 |
| 41 | SMA - 1,000 | 0.64 | PAA - RA-2 | 2.36 | polyethylene glycol lauryl ether (11-120E) | 10 | NaCl | 4 | 1 |
| 42 | SMA - 1,000 | 0.68 | PAA - RA-3 | 2.32 | polyethylene glycol lauryl ether (11-120E) | 10 | NaCl | 4 | 1 |
| 43 | SMA - 1,000 | 1.7 | PAQ - 2 | 1.3 | polyethylene glycol lauryl | 10 | NaCl | 4 | 1 |

TABLE III-continued

| Example No. | POLYMER ANIONIC | % | CATIONIC | % | SURFACE-ACTIVE AGENT | % | ALKALI METAL SALT | % | CATIONIC POLYMER/ ANIONIC POLYMER Equivalents |
|---|---|---|---|---|---|---|---|---|---|
| 44 | Aristoflex A | 2.7 | AZA - 1 | 0.3 | Surfactant ether (11-120E) 10 G | 10 | NaCl | 4 | 1 |
| 45 | Aristoflex A | 1.96 | PAA - RA-3 | 1.04 | Surfactant 10 G | 10 | NaCl | 4 | 1 |
| 46 | Aristoflex A | 2.38 | PAA - RA-3 | 0.62 | Surfactant 10 G | 10 | NaCl | 4 | 0.5 |
| 47 | Aristoflex A | 1.96 | PAA - RA-3 | 1.04 | Surfactant 10 G | 10 | NaCl | 4 | 1 |
| 48 | SMA - 1,000 | 1.2 | PAQ - 1 | 1.76 | Surfactant 10 G | 10 | NaCl | 4 | 1 |
| 49 | GANTREZ ES 425 | 1.54 | PAA - 1 | 1.46 | TA - 3 | 10 | NaCl | 4 | 1 |
| 50 | VERSICOL K 11 | 1.42 | PAQ - 2 | 1.56 | TA - 1 | 10 | NaCl | 4 | 1 |
| 51 | 28 - 29 - 30 | 2.38 | PAA - 1 | 0.62 | Surfactant 10 G | 10 | NaCl | 4 | 1 |
| 52 | Aristoflex A | 1.92 | PAA - RA 2 | 1.08 | Surfactant 10 G | 10 | NaCl | 4 | 1 |
| 53 | Aristoflex A | 2.44 | PAQ - 1 | 0.56 | Surfactant 10 G | 10 | NaCl | 4 | 1 |
| 54 | Aristoflex A | 2.68 | PAQ - 2 | 0.32 | Surfactant 10 G | 10 | NaCl | 4 | 1 |
| 55 | GANTREZ ES 425 | 1.06 | PAA - RA 3 | 1.94 | TA - 5 | 10 | NaCl | 4 | 1 |
| 56 | GANTREZ ES 425 | 1.5 | PAA - 1 | 1.5 | BRIJ 35 | 10 | NaCl | 4 | 1 |
| 57 | GANTREZ ES 425 | 1.05 | PAA - RA 3 | 1.95 | BRIJ 35 | 10 | NaCl | 4 | 1 |
| 58 | ARISTOFLEX A | 2.36 | PAA - 1 | 0.64 | Surfactant 10 G | 10 | NaCl | 4 | 1 |
| 59 | GANTREZ ES 425 | 2.12 | PAQ - 2 | 0.88 | TA - 3 | 10 | NaCl | 4 | 1 |
| 60 | VERSICOL K 11 | 1.44 | PAQ - 2 | 1.56 | TA - 1 | 10 | KCl | 4 | 1 |
| 61 | 28 - 29 - 30 | 2 | PAA - RA 3 | 1 | Surfactant 10 G | 10 | LiCl | 4 | 1 |
| 62 | HYDAGEN F | 2.5 | Polyquart H | 0.5 | AKYPO RLM 100 | 10 | NaCl | 4 | 0.2 |

EXAMPLE 63

The following composition is prepared: Anionic polymer sold under the name

| | |
|---|---|
| VERSICOL K 11 | 1% |
| Cationic polymer referred to as PAQ - 3 | 2% |
| Surface-active agent referred to as TA - 1 | 10% |
| NaCl | 4% |
| Water qsp 100 | |

This composition is used as a shampoo. After application to the hair, it imparts softness to the hair when wet and the hair is easy to comb out.

When dry, the hair has a good hold and a soft feel and is springy and very manageable.

This composition can also be used for restructuring the hair.

Similar results are observed on replacing the surface-active agent referred to as TA-1 by the surface-active agent referred to as TA-2 in this composition, the compounds and their proportions otherwise being the same.

EXAMPLES 64 TO 71

Table IV which follows is intended to illustrate other compositions falling within the scope of the invention; these compositions are homogeneous and impart advantageous cosmetic properties to the hair in the same way as above.

TABLE IV

| Example No. | POLYMER ANIONIC | % | CATIONIC | % | SURFACE-ACTIVE AGENT | % | ALKALI METAL SALT | % | CATIONIC POLYMER/ ANIONIC POLYMER Equivalents |
|---|---|---|---|---|---|---|---|---|---|
| 64 | HYDAGEN F | 1.8 | PAQ - 3 | 1.2 | TWEEN 20 | 10 | NaCl | 4 | 0.44 |
| 65 | HYDAGEN F | 2 | PD 170 | 1 | TA - 1 GLUCAMAT SSE 20 | 8 2 | NaCl | 4 | 0.44 |
| 66 | HYDAGEN F | 1.7 | GAFQUAT 755 | 1.3 | TWEEN 20 | 10 | NaCl | 4 | 0.11 |
| 67 | VERSICOL K 11 | 2 | PAQ - 3 | 1 | TA - 1 | 10 | NaCl | 4 | 0.24 |
| 68 | VERSICOL K 11 | 2 | PAQ - 3 | 1 | AKYPO RLM 100 | 10 | NaCl | 4 | 0.25 |
| 69 | VERSICOL E 5 | 0.5 | CATREX | 2.5 | AKYPO RLM 100 | 10 | NaCl | 4 | |

EXAMPLE 70

A woollen cloth, weighing 127 g/m² and consisting of 20 warp yarns/cm and 17 weft picks/cm, is scoured with methylene chloride.

A sample of this fabric is immersed in a solution having the following composition:

| | |
|---|---|
| Hercosset 57 | 0.5 g |
| Versicol E5 (neutralised to the extent of 100% with NaOH) | 1 g |
| Oxyethyleneated nonylphenol containing 30 mols of ethylene oxide (per mol of phenol) | 1 g |
| NaCl | 4 g |
| Water qsp | 100 g |

The pH is adjusted to 7 with HCl and the ratio of equivalents of cationic units to equivalents of anionic units (CP/AP equivalents) is 0.4.

The liquor ratio is 1/40 and the whole is kept at ambient temperature for 15 minutes. The sample is rinsed with running water and then dried in an oven at 60° C.

This sample of fabric is characterised by a much greater stiffness than that of control samples treated solely with a solution of cationic polymer at the concentration and the pH at which the polymer is present in the treatment bath.

EXAMPLE 71

A sample of woollen cloth, weighing 127 g/m², is scoured with methylene chloride and then chlorinated at ambient temperature using a liquor ratio of 1/100. 1 g of scoured wool is introduced into a mixture of 100 ml of water and 0.1 ml of analytical grade HCl. After an impregnation time of 5 minutes, 4 ml of Javelle water of 45° strength of active chlorine are added and this is allowed to act for 30 minutes.

2 ml of sodium bisulphite solution are then added and rinsing with running water is carried out after 15 minutes. This sample is immersed, as in Example 70, in a composition comprising

| | |
|---|---|
| Polymer referred to as PAQ-3 | 1 g |
| Hydagen F | 1 g |
| Surface-active agent TA-1 | 1 g |
| NaCl | 5 g |
| Water qsp | 100 g |
| The pH is adjusted to 7 with HCl. | |

The ratio of equivalents of cationic units to equivalents of anionic units is equal to 0.7.

After treatment, the sample is characterised by a very marked stiffness.

EXAMPLE 72

A woollen fabric, weighing 127 g/m², scoured with methylene chloride and then chlorinated as indicated in Example 71, is neutralised with a 20% strength solution of sodium carbonate and then rinsed with running water.

This sample is immersed, as in Example 70, in a composition comprising:

| | |
|---|---|
| MERQUAT 100 | 1 g |
| VERSICOL E5 (neutralised to the extent of 100% by NaOH) | 1.5 g |
| Oxyethyleneated nonylphenol containing 30 mols of ethylene oxide | 1 g |
| NaCl | 4 g |
| Water qsp | 100 g |
| The pH is adjusted to 7 with HCl. | |

The ratio of equivalents of cationic units to equivalents of anionic units is equal to 0.4.

A greater stiffness of the wool treated is also observed in this case.

Similar results to those mentioned above are obtained on impregnating the fabric in the various compositions using a liquor ratio of 1/40 in a bath which can be hot or cold. The fabric is squeezed off to a pickup of about 70% and optionally dried in an oven at 60°.

The drying can also be effected by placing the fabric in an oven for 10 minutes at 120°.

EXAMPLES 73 TO 76

On washing the treated wool, as mentioned in Examples 70 to 72, by means of the following compositions;

| Example | Anionic polymer | % | Cationic polymer | % | Surface-active agent | % | Alkali metal salt | % | CP/AP Equivalents |
|---|---|---|---|---|---|---|---|---|---|
| 73 | Gantrez ES 425 | 2.5 | AZA - 1 | 0.5 | TA - 1 | 12.5 | NaCl | 4 | 0.5 |
| 74 | SMA 1,000 | 1.10 | AZA - 1 | 1.9 | TA - 2 | 10 | NaCl | 4 | 0.4 |
| 75 | GANTREZ ES 425 | 0.46 | PAA - RA3 | 2.54 | TA - 1 | 12.5 | NaCl | 4 | 3 |
| 76 | VERSICOL K 11 | 1.44 | PAQ - 2 | 1.56 | TA - 1 | 10 | KCl | 4 | 1 | and on rinsing with running water, an increase in the firmness of the wool is observed.

EXAMPLES 77 TO 82

These Examples illustrate the treatment of fibres and fabrics, as indicated below, with a homogeneous aqueous composition containing (1) a cationic polymer, (2) an anionic polymer, (3) an alkali metal salt and (4) a surface-active agent.

| FIBRES: | | |
|---|---|---|
| Polypropylene 2.5 D Montedison | | |
| Polyester CHEROTAN 3 D/60 | | |
| FABRICS: | | |
| White test fabric | NYLON | (Polyamide 6.6) |
| White test fabric | TERGAL | (Polyester) |
| White test fabric | CRYLOR | (Polyacrylonitrile) |
| White test fabric | THERMOVYL | (Polyvinylchloride) |
| White test fabric | RILSAN | (Polyamide 11) |
| White test fabric | TRIACETATE | |
| White test fabric | VISCOSE | |
| Fabric | 100% COTTON | (weight 163g/m², 29 wefts per cm, 52 yarns per cm). |
| Fabric | 55% wool 45% polyester | (weight 324g/m², 20 wefts per cm, 35 yarns per cm). |

Before the treatment, the fibres and fabrics were washed with a solution containing 2% of detergent (Coptal BR sold by UGINE KUHLMAN), rinsed copiously with running water then dried at ambient temperature.

APPLICATION OF THE COMPOSITIONS

The test fibres and fabrics were immersed in the composition (ratio of bath 40:1) at ambient temperature for 15 minutes. Part of the test materials were rinsed and the other part was not rinsed but excess liquid was squeezed out between a series of rollers and then the test materials were dried.

In some cases the drying was followed by a thermal treatment at a temperature and for a duration compatible with the properties of the materials and polymers used.

EXAMPLE 77

| | |
|---|---|
| PAA-R I | 3 g |
| GANTREZ ES 425 completely neutralised with NaOH | 3 g |
| TA 1 | 1 g |
| Na Cl | 3 g |
| Water q.s.q. | 100 g |
| pH = 8 | |

FABRICS

The fabrics were immersed in the composition for 15 minutes at ambient temperature with a bath ratio of 40:1. Half the test materials were then rinsed with running water and the other half were not rinsed but squeezed out (degree of squeezing out 70%). All the fabrics were dried in an apparatus with forced air at 60° C. for 30 minutes.

The following results were observed:

100% Cotton fabric:

With or without rinsing an increase in the rigidity of the fabric was noted. The effect was more marked however without rinsing. This rigidity is superior to that which is achieved using each of the polymers separately from a solution containing the same products as in the mixture used.

Wool/polyester fabric:

Same results as above although the increase in the rigidity was more marked than with the cotton fabric.

100% Nylon fabric:

Results identical to those above. The effect is the same degree as with cotton.

100% Viscose fabric:

Very clear results and of the same type as those above. The effect is very marked when no rinsing takes place.

Crylor fabric:

The effect is very marked, more marked than for the nylon and viscose. It is practically the same whether or not the fabric has been rinsed.

FIBRES

Cherotan polyester:

Very slight increase in rigidity of a sample of fibres which appear denser and more compact when the composition is not rinsed.

Polypropylene:

Identical results to those obtained on the polyester.

EXAMPLE 78

| | |
|---|---|
| CARTARETINE F4 | 0.5 g |
| MERQUAT 100 | 0.25 g |
| VERSICOL E 5 | 0.5 g |
| Na Cl | 3 g |
| TA 2 | 10 g |
| Water q.s.p. | 100 g |
| pH = 9.1 (Na OH) | |

This composition applied to a 100% Crylor fabric gave a very slight increase in rigidity. The effect is comparable whether or not the material is subsequently rinsed.

EXAMPLE 79

| | |
|---|---|
| CARTARETINE F4 | 5 g |
| MERQUAT 100 | 2.5 g |
| VERSICOL E 5 | 0.5 g |
| Na Cl | 5 g |
| NIC 33 | 5 g |
| Water q.s.p. | 100 g |
| pH = 9.1 (Na OH) | |

This composition applied to a 100% Crylor fabric led to a very slight increase in rigidity. The effect is a little more marked when the fabric is not subsequently rinsed.

EXAMPLE 80

| | |
|---|---|
| PD 170 | 0.65 g |
| GANTREZ ES 425, 100% neutralised with NaOH | 1 g |
| Na Cl | 5 g |
| SANDOPAN DTC acid | 5 g |
| Water q.s.p. | 100 g |
| pH = 8.9 (Na OH) | |

This composition applied to a 100% cotton fabric led to a very slight increase in rigidity when the application was not followed by rinsing. The same result was obtained on drying the fabric to a 100° C. in an oven.

EXAMPLE 81

| | |
|---|---|
| POLYMIN HS | 1 g |
| VERSICOL E 5 | 3 g |
| Na Cl | 5 g |
| AKYPO RLM 100 | 2.5 g |
| Water q.s.p. | 100 g |
| pH = 9.1 (Na OH) | |

This composition was applied to wool polyester fabric (55/45) and it gave a very slight increase in rigidity when the application was not followed by rinsing. The same result was obtained on drying the fabric at 100° C. in an oven or subjecting the already dried material to a subsequent thermal treatment at 100° C. for 10 minutes.

EXAMPLE 82

| | |
|---|---|
| POLYMIN HS | 3 g |
| DARVAN No. 7 | 3 g |
| Na Cl | 3 g |
| NI 170 | 1 g |
| Water q.s.p. | 100 g |
| pH = 9.5 (Na OH) | |

This composition applied to a 100% tergal fabric gave a very slight increase in rigidity. The effect was more marked when the application was not followed by rinsing.

The various abbreviations and tradenames, used in the above Examples are explained in greater detail below.

ANIONIC POLYMERS

GANTREZ ES 425 Poly-(methyl vinyl ether/maleic acid) monobutyl ester sold by GENERAL ANILINE.

28-29-30 Vinyl acetate/crotonic acid/vinyl neodecanoate terpolymer sold by NATIONAL STARCH.

ARISTOFLEX A Terpolymer of vinyl acetate/crotonic acid and polyethylene glycol sold by HOECHST.

VERISICOL K 11 Methacrylic acid polymer having a molecular weight of 10,000 and a viscosity of 1,000 cps in a 25% strength solution, sold by ALLIED COLLOIDS.

VERSICOL E 5 Mixture of acrylic acid homopolymer and copolymer, having a viscosity of 16 cps in a 25% strength solution and a molecular weight of about 3,500, sold by ALLIED COLLOIDS.

SMA-1,000 Styrene/maleic anhydride copolymer having a mean molecular weight of 1,600 and a viscosity of 17 cps in 15% strength aqueous ammonia, sold by ARCO CHEMICAL CO.

DARVAN No. 7 Sodium polymethacrylate sold by VAN DER BILT.

CATIONIC POLYMERS

AZA-1: Cationic product resulting from the polycondensation of piperazine, diglycolamine and epichlorohydrin in the molar proportions of 4/1/5, described in Example 2 of French Pat. No. 2,280,301.

AZA-2: Cationic product resulting from the polycondensation of bis-(chloroacetyl)-piperazine and piperazine in equimolecular amounts.

PAA-1: Product resulting from the polycondensation of adipic acid and diethylenetriamine in equi-molecular amounts.

PAA-2: Product resulting from the polycondensation, with diethylenetriamine, of the product resulting from the reaction of 2 mols of methyl itaconate and 1 mol of ethylenediamine.

PPA-R1: Polymer resulting from the crosslinking of the polymer PAA-1 with epichlorohydrin (11 molecules of epichlorohydrin per 100 amine groups).

PPA-R2: Polymer obtained by crosslinking the polymer PAA-1 with a random oligomeric crosslinking agent of the formula $$\left[ ClCH_2-CHOH-CH_2 \left[ N \bigcirc N-CH_2-CHOH-CH_2 \right]_2 Cl \right]$$

PAA-RA1: Polymer resulting from the alkylation of the polymer PAA-R1 with tert.-butyl glycidyl ether.

PAA-RA2: Polymer resulting from the alkylation, with glycidol, of the polymer referred to as PAA-R 1.

PAA-RA3: Polymer resulting from the alkylation of the polymer PAA R1 with glycidyltrimethylammonium chloride.

This polymer is prepared in accordance with the following process:

158 g (that is to say 1,000 meq of epoxide) of glycidyltrimethylammonium chloride are added to 1,314 g of PAA-R1 in a 20% strength aqueous solution (1,123 meq of basicity). The mixture is heated for 2 hours at 60° C. and then diluted with 2 liters of water.

The mixture is kept at 60° C. for a further 2 hours.

A yellow solution containing 11.8% of active ingredient is obtained.

Characteristics of the solution:

Chlorine number = 0.34 meq/g

Base number: 0.29 meq/g

Viscosity (in a solution containing 10% of active ingredient) at 25° C.: 0.24 poise for a velocity gradient of 14.7 second$^{-1}$.

PAQ-1: Polymer having recurring units of the formula $$\left[ \begin{array}{c} CH_3 \\ | \\ -N-(CH_2)_3-N-CH_2-CONH-(CH_2)_2-NHCO-CH_2- \\ \oplus | Cl^\ominus \quad \oplus | Cl^\ominus \\ CH_3 \quad\quad CH_3 \end{array} \right]$$

PAQ-2: Polymer having recurring units of the formula $$\left[ \begin{array}{c} CH_3 \quad\quad CH_3 \\ | \quad\quad\quad | \\ -N^\oplus-(CH_2)_3-N^\oplus-(CH_2)_6- \\ | \quad\quad\quad | \\ CH_3 \quad\quad CH_3 \\ Cl^\ominus \quad\quad Cl^\ominus \end{array} \right]$$

PAQ-3: Polymer having recurring units of the formula $$\left[ \begin{array}{c} CH_3 \quad\quad O \quad\quad\quad CH_3 \\ | \quad\quad\quad || \quad\quad\quad | \\ -N-(CH_2)_3-NH-C-NH-(CH_2)_3-N-(CH_2)_2-O-(CH_2)_2 \\ | \quad\quad\quad\quad\quad\quad\quad\quad\quad\quad | \\ CH_3 \quad\quad\quad\quad\quad\quad\quad\quad CH_3 \end{array} \right] \begin{array}{c} 2n + \\ 2nCl^- \end{array}$$

n being equal to about 6.

GAFQUAT 755: Quaternary vinylpyrrolidone copolymer having a molecular weight of 1,000,000, marketed by GENERAL ANILINE.

MERQUAT 550: Dimethyldiallylammonium chloride/acrylamide copolymer having a molecular weight > 500,000, sold by MERCK.

PD 170: Adipic acid/epoxypropyl-diethylenetriamine copolymer sold by HERCULES, of the formula $$\left[ \begin{array}{c} +C+(CH_2)_4-C-NH(CH_2)_2-\overset{+}{N}-(CH_2)_2-NH \\ || \quad\quad\quad || \\ O \quad\quad\quad O \quad\quad\quad\quad\quad \bigcirc \\ \quad\quad\quad\quad\quad\quad\quad\quad\quad OH \end{array} \right]_n Cl^-$$

POLYQUART H: Polyglycol-polyamine polycondensate sold by HENKEL.

CARTARETINE F4: Adipic acid/dimethylaminohydroxypropyldiethylenetriamine copolymer sold by SANDOZ.

MERQUAT 100: Dimethyldialyl ammonium homopolymer of molecular weight below 100,000 sold by MERCK.

POLYMIN H.S.: Polyethyleneimine of $d_{20}$ = about 1.07 and viscosity 500–1,000 cps as a 20% aqueous solution sold by BASF.

SURFACE ACTIVE AGENTS

TA-1:

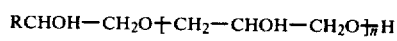

R: $C_9$–$C_{12}$ alkyl; n = 3.5.

TA-2: Non-ionic surface-active agent based on polyglycerolated (4.2 mols) lauryl alcohol in a solution containing about 60% of active ingredient. Formula (statistical):

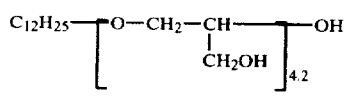

TA-3: Surface-active agent of the statistical formula:

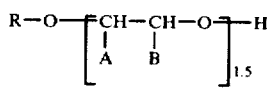

R: $C_{12}$–$C_{14}$ alkyl; one of A and B denotes hydrogen and the other denotes:

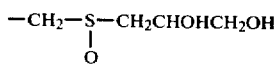

TA-4: Surface-active agent of the formula:

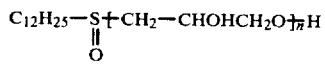

n has the statistical value 2.5.

TA-5: Polyglycerolated derivative of TA-4, containing 3 mols of glycerol.

SURFACTANT 10 G: Nonylphenyl polyglyceryl ether (10 glyceryloxy units).

BRIJ 35: Polyethylene glycol lauryl ether containing 23 mols of ethylene oxide.

AKYPO RLM 100: R-(OCH$_2$CH$_2$)$_z$OCH$_2$COOH$_2$O R being a mixture of $C_{12}$–$C_{14}$ alkyl radicals and z being equal to 10, sold by CHEMY.

TWEEN 20: Polyoxyethyleneated sorbitan monolaurate containing 20 mols of ethylene oxide, sold by ATLAS.

GLUCAMAT SSE 20: Polyoxyethyleneated sucrose stearate containing 20 mols of ethylene oxide.

SANDOPAN DTC acid of the formula: CH$_3$—(CH$_2$)$_{12}$—(OCH$_2$CH$_2$)$_6$—OCH$_2$—COOH sold by SANDOZ.

NIC 33: Non-ionic surface-agent of the formula:

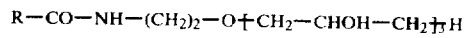

R = a mixture of $C_{12}$–$C_{18}$ radicals derived from coprah.

We claim:

1. A composition suitable for the treatment of fibrous materials which is in the form of an aqueous composition containing at least one cationic polymer which is a polyamine or quaternary polyammonium polymer in which the amine or ammonium group forms part of the polymer chain or is joined to the latter, at least one anionic polymer containing carboxylic groups, at least one alkali metal salt and at least one surface-active agent, the only surface-active agents in the composition being surface-active agents which are either non-ionic or contain one or more carboxyl or carboxylate groups in addition to one or more non-ionic groups, the cationic polymer and the anionic polymer each being present in an amount from about 0.25 to 3% by weight, the at least one surface-active agent being present in an amount from about 1 to 50% by weight, and the alkali metal salt being a halide, sulfate, acetate or lactate.

2. A composition according to claim 1 which has a pH of 5 to 8.

3. A composition according to claim 1 or 2 in which the alkali metal salt is present in an amount from 0.25 to 8% by weight.

4. A composition according to claim 1 or 2 in which the ratio of anionic polymer to cationic polymer is from 5:1 to 0.04:1, expressed as the ratio of equivalents of cationic units to the equivalents of anionic units.

5. A composition according to claim 1 or 2 in which the alkali metal salt is a potassium, sodium or lithium salt.

6. A composition according to claim 1 or 2 in which the anionic polymer contains units derived from an unsaturated mono- or di-carboxylic acid of the formula

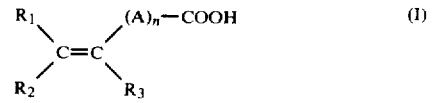

in which n is 0 or an integer from 1 to 10; A denotes a methylene group which is joined to the carbon atom of the unsaturated group and/or to the adjacent methylene group if n is greater than 1, either directly or via a hetero-atom; R$_1$ denotes a hydrogen atom or a phenyl or benzyl group; R$_2$ denotes a hydrogen atom or an alkyl group of 1 to 4 carbon atoms or a carboxyl group; and R$_3$ denotes a hydrogen atom, an alkyl group of 1 to 4 carbon atoms, a CH$_2$-COOH group or a phenyl or benzyl group.

7. A composition according to claim 1 or 2, in which the cationic polymer is an optionally quaternised vinylpyrrolidone/aminoalcohol acrylate copolymer or a cellulose ether derivative containing quaternary ammonium groups.

8. A composition according to claim 1 or 2 in which the cationic polymer is selected from:

(1) a water-soluble cyclic polymer having a molecular weight of 20,000 to 3,000,000 and containing chain units of the formula (II) or (II'):

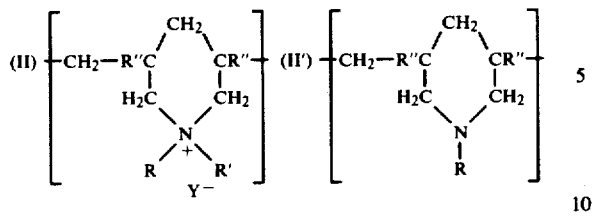

in which R" denotes hydrogen or methyl, R and R' independently denote an alkyl group having from 1 to 22 carbon atoms, a hydroxyalkyl group or a lower amidoalkyl group, or R and R' together denote, with the nitrogen atom to which they are attached, a heterocyclic group and $Y^-$ denotes a bromide, chloride, acetate, borate, citrate, tartrate, bisulphate, bisulphite, sulphate or phosphate anion (2) an acrylic acid or methacrylic acid homopolymer or copolymer comprising the chain unit:

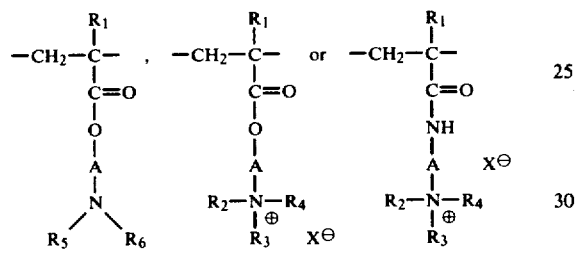

in which $R_1$ is H or $CH_3$; A is a linear or branched alkyl group having 1 to 6 carbon atoms or a hydroxyalkyl group having 1 to 4 carbon atoms; $R_2$, $R_3$ and $R_4$, independently denote an alkyl group having 1 to 18 carbon atoms or a benzyl group; $R_5$ and $R_6$ independently denote H or alkyl having 1 to 6 carbon atoms, and $X^\theta$ denotes a methosulphate or halide anion (3) a cationic polymer having recurring units of the formula: -A-Z-A-Z- (III), in which A denotes a radical containing 2 amino groups and Z denotes the symbol B or B' and B and B', which are identical or different, denote a linear or branched alkylene radical which is unsubstituted or substituted by one or more hydroxyl groups and which can contain 1 to 3 aromatic and/or heterocyclic rings as well as oxygen, nitrogen and sulphur atoms; or having recurring units of the formula: $-A-Z_1-A-Z_1-$ (IV), in which A is as defined above and each $Z_1$ independently denotes $B_1$ or $B'_1$ such that at least one Z denotes $B'_1$, $B_1$ denotes a linear or branched alkylene or hydroxyalkylene radical having up to 7 carbon atoms in the main chain and $B'_1$ denotes a linear or branched alkylene radical having up to 7 carbon atoms in the main chain and is unsubstituted or substituted by one or more hydroxyl radicals and contains one or more chain nitrogen atoms which are substituted by an alkyl chain which optionally contains one or more chain oxygen atoms and one or more hydroxyl and/or carboxyl groups; or a quaternary ammonium salt of a polymer of formula (III) or (IV) or an oxidation product of a polymer of formula (III) or (IV) such that at least one tertiary amino group in A has been converted into an amine oxide group (4) a quaternary polyammonium compound of the formula:

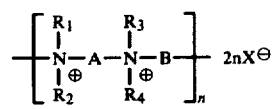

in which $R_1$, $R_2$, $R_3$ and $R_4$, which are identical or different, represent an aliphatic, alicyclic or arylaliphatic radical containing a maximum of 20 carbon atoms, or a lower hydroxyaliphatic radical, or $R_1$ and $R_2$, and/or $R_3$ and $R_4$, together form, with the nitrogen atom to which they are attached, a heterocyclic ring optionally containing a second heteroatom other than nitrogen, or $R_1$, $R_2$, $R_3$ and $R_4$ independently represent a group of formula:

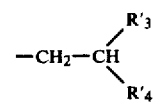

in which $R'_3$ denotes hydrogen or lower alkyl and $R'_4$ denotes —CN,

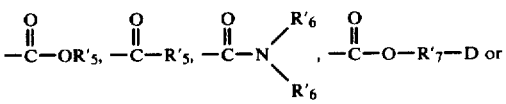

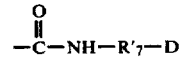

in which $R'_5$ denotes lower alkyl, $R'_6$ denotes hydrogen or lower alkyl, $R'_7$ denotes alkylene and D denotes a quaternary ammonium group, A and B independently represent a linear or branched saturated or unsaturated aliphatic group of 2 to 20 carbon atoms, which contain in the chain one or more aromatic rings, and/or one or more groups of formula $-CH_2-Y-CH_2-$, in which Y denotes O, S, SO, $SO_2$,

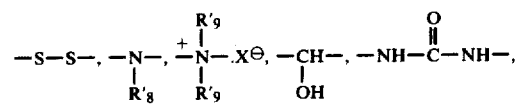

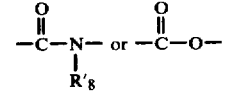

in which $X^\ominus$ denotes an anion of an inorganic or organic acid, $R'_8$ denotes hydrogen or lower alkyl and $R'_9$ denotes lower alkyl, or A, $R_1$ and $R_3$ form a piperazine ring together with the two nitrogen atoms to which they are attached, and B can also denote a group of formula: $-(CH_2)_nCO-D-OC-(CH_2)_n-$, in which D denotes:

(a) a glycol radical of the formula -O-Z-O-, in which Z denotes a linear or branched hydrocarbon radical or a group of the formula:

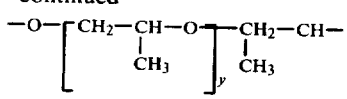

in which x and y independently denote an integer from 1 to 4;

(b) a bis-secondary diamino radical;

(c) a bis-primary diamino radical of the formula: -NH-Y-NH-, in which Y denotes a linear or branched hydrocarbon radical or the divalent radical -CH$_2$-CH$_2$-S-S-CH$_2$-CH$_2$-; or (d) a ureylene group of the formula -NH-CO-NH-; and n is such that the molecular weight is from 1,000 to 100,000

(5) a polyaminoamide (6) a crosslinked polyaminoamide which is:

(a) water-soluble, optionally alkylated, crosslinked polyaminoamide obtained by crosslinking a polyaminoamide derived from the polycondensation of an acid compound with a polyamine, with a crosslinking agent which is an epihalogenohydrin, diepoxide, dianhydride, unsaturated anhydride or a bis-unsaturated derivative, in an amount from 0.025 to 0.35 molecules per amine group of the polyaminoamide, (b) a water-soluble, crosslinked polyaminoamide derived by crosslinking a polyaminoamide as defined above, with a crosslinking agent which is:

I a bis-halogenohydrin, bis-azetidinium compound, bis-halogenoacyl diamine or a bis-(alkyl halide), II an oligomer obtained by reacting a compound from group I, or an epihalogenohydrin, diepoxide or bis-unsaturated derivative, with a difunctional compound or III a product resulting from the quaternisation of a compound from group I or an oligomer from group II which contain one or more tertiary amine groups which can be alkylated with an alkylating agent, in an amount from 0.025 to 0.35 molecule of crosslinking agent per amine group of polyaminoamide, (c) a water-soluble polyaminoamide derivative resulting from the condensation of a polyalkylenepolyamine with a polycarboxylic acid and alkylation of the condensate with a difunctional agent (7) a polymer obtained by reacting a polyalkylenepolyamine, containing two primary amine groups and at least one secondary amine group, with a dicarboxylic acid which is diglycolic acid or a saturated aliphatic dicarboxylic acid having 3 to 8 carbon atoms, the molar ratio of the polyalkylenepolyamine to the dicarboxylic acid being from 0.8:1 and 1.4:1 and the resulting polyamide being reacted with epichlorohydrin in a molar ratio of epichlorohydrin to the secondary amine group of the polyamide of 0.5:1 to 1.8:1, (8) an optionally alkylated or alkoxylated polyalkyleneimine, (9) a product resulting from the condensation of a polyamine with epichlorohydrin,

(10) a quaternary polyureylene.

9. A composition according to claim 1 or 2 in which the non-ionic surface-active agent is condensation product of monoalcohol, an alpha-diol, an alkylphenol or an alkylamide with glycidol; a polyoxyethyleneated alcohol or alkylphenol, or an ester of a polyethylene glycol or polyglycerol with a linear fatty chain having 8 to 18 carbon atoms; a copolymer of ethylene oxide and propylene oxide, or a condensation product of ethylene oxide and propylene oxide with a fatty alcohol; a polyoxyethyleneated fatty amide; a polyoxyethyleneated fatty amine; or a polyoxyethyleneated fatty acid ester of sorbitol or of sucrose.

10. A composition according to claim 1 or 2 in which the non-ionic surface-active agent is a compound of the formula:

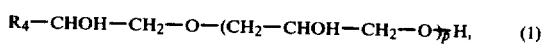

in which R$_4$ denotes an aliphatic, cycloaliphatic or arylaliphatic radical having 7 to 21 carbon atoms, which can contain an ether, thioether, or hydroxymethylene group, and p is from 1 to 10; or

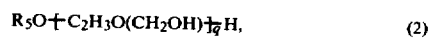

in which R$_5$ denotes an alkyl, alkenyl or alkylaryl radical and q is from 1 to 10; or

in which R$_6$ denotes a linear or branched, saturated or unsaturated, aliphatic radical having 8 to 30 carbon atoms, which can contain one or more hydroxyl groups, and r is from 1 to 5.

11. A composition according to claim 1 or 2 in which the surface-active agent containing one or more carboxyl or carboxylate groups in addition to non-ionic groups is a polyglyceryl carboxylate or carboxylic acid of a polyglycol ether, of the formula Alk—(OCH$_2$CH$_2$-)$_n$—OCH$_2$CO$_2$H, in which Alk denotes a linear chain having 12 to 18 carbon atoms and n is from 5 to 15, or a salt thereof.

12. A composition according to claim 1 or 2 which contains one or more of an organic solvent, thickener, dyestuff, perfume, preservative, natural product, sequestering agent, emulsifier, softener, synergistic agent or foam stabiliser.

13. Process for treating fibrous material which comprises applying thereto a composition as defined in claim 1.

14. Process according to claim 13 in which after the application water is bonded to the material to deposit the polymer onto the material.

15. Process according to claim 13 for treating human hair in which the composition is in the form of a shampoo, a colouring product, a rinsing lotion intended to be applied before or after shampooing, before or after colouring or bleaching or before or after permanent waving, a brushing lotion or a restructuring lotion.

* * * * *